United States Patent [19]

Fraser et al.

[11] Patent Number: 4,667,520

[45] Date of Patent: May 26, 1987

[54] DYNAMOMETER ARRANGEMENT

[75] Inventors: Gregory A. Fraser, Montreal; Simon Raab, Lorraine, both of Canada

[73] Assignee: Orthotronics Limited Partnership, Canada

[21] Appl. No.: 805,123

[22] Filed: Dec. 4, 1985

Related U.S. Application Data

[63] Continuation-in-part of Ser. No. 734,980, May 16, 1985, abandoned.

[51] Int. Cl.[4] .................................................. G01L 5/16
[52] U.S. Cl. ..................................... 73/862.04; 73/172
[58] Field of Search ........... 73/862.04, 862.05, 862.06, 73/65, 172

[56] References Cited

U.S. PATENT DOCUMENTS

| | | | |
|---|---|---|---|
| 2,860,514 | 11/1958 | Lauru | 73/379 |
| 3,921,445 | 11/1975 | Hill et al. | 73/862.04 |
| 3,939,704 | 2/1976 | Zipin | 73/862.04 |
| 4,178,799 | 12/1979 | Schmieder et al. | 73/862.04 |
| 4,550,617 | 11/1985 | Fraignier et al. | 73/862.04 |

*Primary Examiner*—Charles A. Ruehl
*Attorney, Agent, or Firm*—Fishman & Dionne

[57] ABSTRACT

The spaced beam and bearing arrangements each comprise a deflection beam and a support. The platform is disposed on and supported by the support for receiving and being deflected by an applied force. Thus, deflection of the platform is transmitted to the deflection beams to cause deflection of the deflection beams. The beam and bearing arrangements isolate beam deflections to two mutually perpendicular directions, which mutually perpendicular directions are both perpendicular to the longitudinal axis of each deflection beam. The deflection of the deflection beams is measured in the two directions thereof and the deflection beams are arranged such that no two redundant directions of the deflection beams are permissible.

7 Claims, 17 Drawing Figures

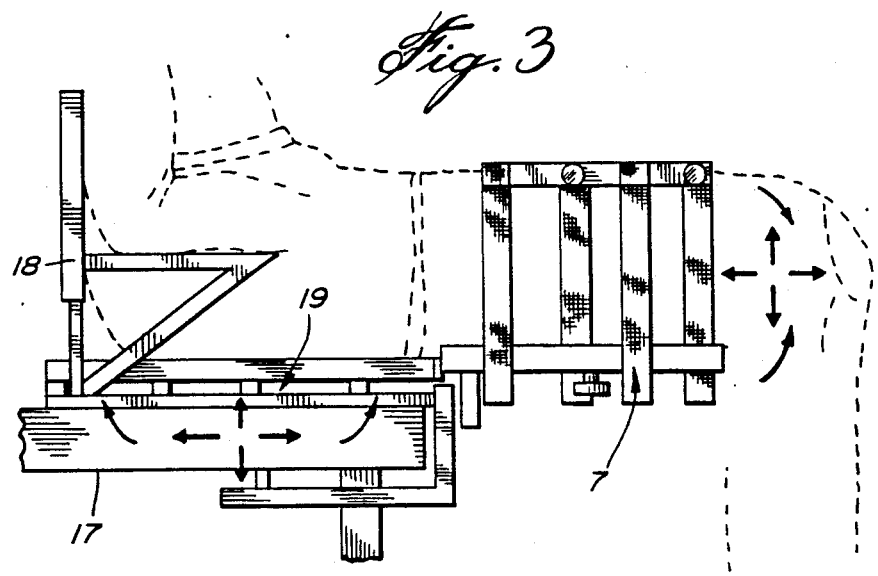
Fig. 3
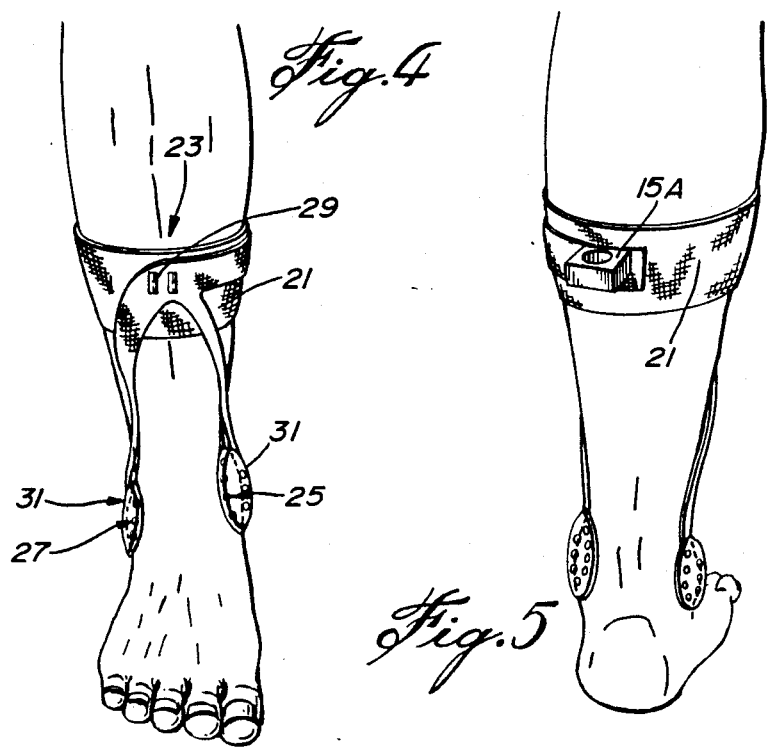
Fig. 4
Fig. 5

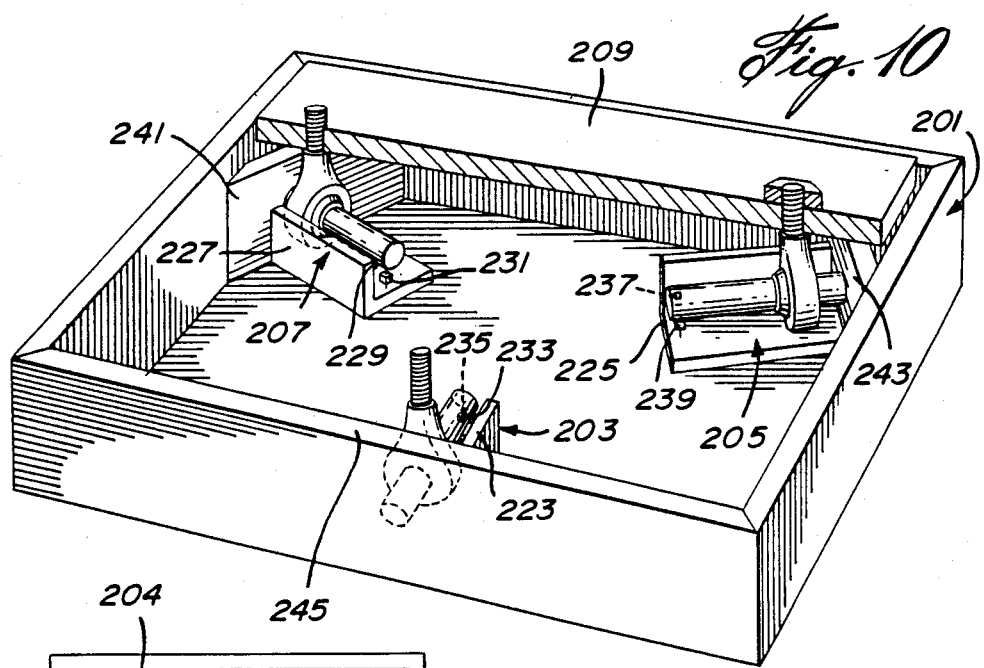
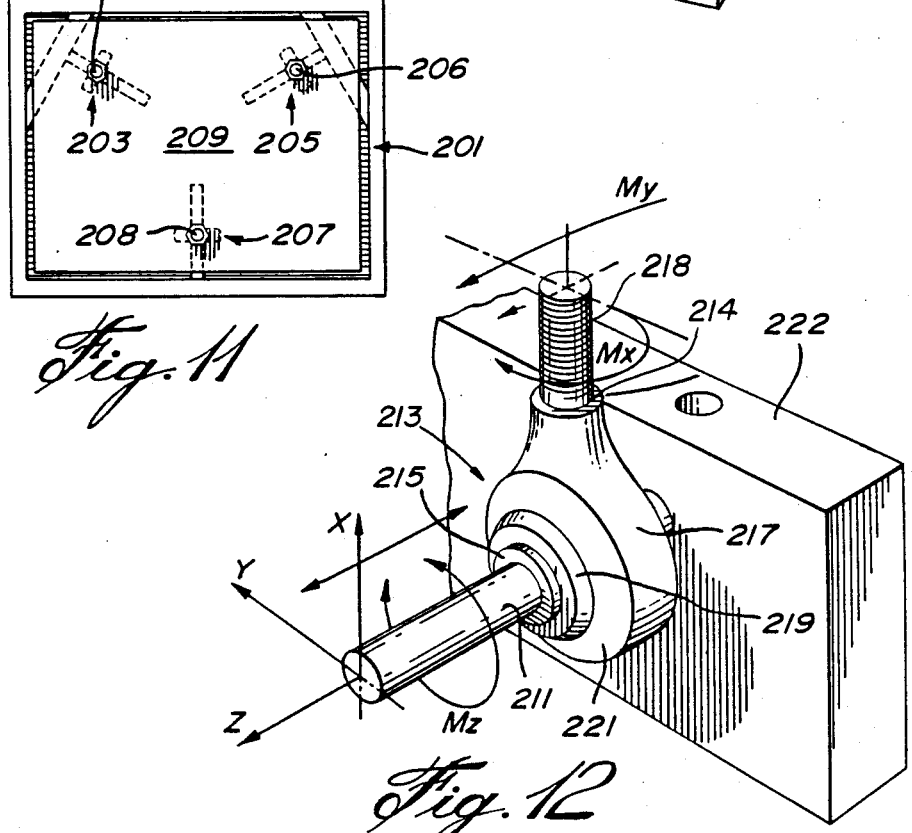

DYNAMOMETER ARRANGEMENT

CROSS REFERENCE TO RELATED APPLICATION

This is a C-I-P of parent application Ser. No. 734,980, filed May 16, 1985, now abandoned.

BACKGROUND OF INVENTION (a) Field of the Invention

The invention relates to a novel knee laxity evaluator (KLE) system.

The invention also relates to a motion module/digitizer combination which can be used in the KLE, or which can be used independently or in other systems. More specifically, the invention relates to such a combination which can measure, in three dimensional space, and relative to the position of a first point or body or co-ordinate system, position or motion of a second point or body, as well as position or motion of the second point or body relative to a thrid, fourth, fifth . . . nth points, or positions of the second body, or combinations thereof.

(b) Description of the Prior Art

Currently, the practice of measuring knee laxity is limited to a subjective evaluation by a physician of relative displacements at the knee. Through such an examination, damage to ligaments could be ascertained as a function of excess laxity or joint movement during passive loading by the physician. The limitations of this technique are: (a) a high level of subjectiviey; (b) no quantitative or reproducible results; (c) no knowledge of applied forces; and (d) there are complicated motions which cannot be evaluated by human feel alone and hence there is important information being lost.

In accordance with the present invention, a KLE includes a motion module, that is, a module for measuring, in three dimensional space, movement of a point or body relative to a fixed point or body. Modules of this type are known in the art as is illustrated, for example, in U.S. Pat. No. 3,944,798, Eaton, Mar. 16, 1976, U.S. Pat. No. 4,057,806, Furnadjiev et al, Nov. 8, 1977, and U.S. Pat. No. 4,205,308, Haley et al, May 27, 1980.

Electrical and electronic digitizers are also known in the art. For example, a two dimensional digitizer is illustrated in U.S. Pat. No. 3,956,588, Whetstone et al, May 11, 1976.

However, there are no teachings in the art for combining the first systems, usually referred to as motion modules, and digitizers, whereby it is possible to measure the position or motion of a second point or body relative to the position of a first point or body and also relative to third, fourth, fifth . . . nth points or positions of the second body or combinations thereof.

Also in accordance with the present invention a KLE includes a force dynamometer, that is, a device for measuring external forces and moments applied to a body.

Force dynamometers are known in the art and are often referred to as multi-axis load cells, for example in U.S. Pat. No. 4,092,854, Henry et al, Apr. 20, 1977. Multi-axis load cells which have been previously described suffer from one or more of the following drawbacks:

1. Poor resolution
2. Hysteresis
3. Use of greater than the minimum six transducers inherently required to resolve the force and moment components
4. Cross influencing between the various transducers.

With the exception of the drawback of using more than the minimum six transducers required the other problems listed generally result from the construction of the load cells. The problem has been to provide a structurally stable load cell while at the same time permitting one unique set of six transducer outputs for a given externally applied force and/or moment. In the above-mentioned reference, for example, the arrangement of flexure arms and flexure beams reduces, but does not eliminate cross influencing of combined load signals. If for example, a combined load were applied resulting in the flexion of a flexure arm about an axis through its center, parallel to the primary Z-axis, this load would be picked up not only in the six transducers but some would be "lost" by being absorbed in the chassis, through the flexure arms, and thus not transmitted to the transducers.

SUMMARY OF INVENTION

It is therefore an object of the invention to provide a novel knee laxity evaluator system.

It is a further object of the invention to provide a knee laxity evaluator system which uses a motion module.

It is a still further object of the invention to provide a combined electronic motion module/digitizer combination which can be used in the KLE or which can be used independently or in other systems.

It is a more specific object of the invention to provide such a combination which will measure, in three dimensional space, and relative to the position of a first point or body, position or motion of a second point or body as well as position or motion of the second point or body relative to the third, fourth, fifth . . . nth points, or positions of the second body or combinations thereof.

It is a still further object of the invention to provide a novel dynamometer which can be used in the KLE or which can be used independently.

Therefore it is an object of the present invention to produce a dynamometer or a multi-axis load cell of a type described in which the cross influencing between various transducers is effectively eliminated, by ensuring that the only resistance which can be supplied to an external force by the dynamometer is in the directions independently measured by the six transducer elements.

In accordance with a particular embodiment of the invention, a knee laxity evaluator comprises an instrumented seat for seating a patient and restraint means for restraining a portion of the patient to the instrumented seat whereby to measure forces applied to the patient at an unrestrained part thereof. Motion module means measure the motion of the unrestrained part of the patient relative to the restrained part thereof, and processor means analyze outputs of the instrumented seat and the motion module means and provide indications of applied force and motion of the unrestrained part relative to the restrained part.

From a different aspect, and in accordance with the invention, a motion module/digitizer combination comprises an elongated member having a first end and a second end and comprising a first link arm and a second link arm and means movably connecting the first link arm to the second link arm so as to permit translational motion between the first end and the second end, the means for connecting being disposed intermediate the first and second ends, the means also including first transducer means for measuring the translational motion. First mounting means are provided at the first end for mounting the first end at a first point, body or coordinate system and second mounting means are provided at the second end for mounting the second end at a second point or body. Second transducer means are provided at the first end for measuring three dimensional rotational motion of the first link arm relative to the first point or body and a third transducer means is provided at the second end for measuring three dimensional rotational motion of the second link arm relative to the second point or body. In accordance with the invention, a portion of the second link arm is detachable from the remainder of the second link arm and the second mounting means and means are connectable to the remainder of the second link arm. Whereby, the combination of the first link arm, the remainder of the second link arm, and the means connectable, can be used to measure the position in space of third, fourth, fifth . . . nth points or combinations thereof. And whereby, when the remainder of the link arm is reattached to the portion of the second link arm and the second mounting means, measurements can be performed to determine the position in space of the second point or body relative to the position of the first point or body or the position in space of the second point or body relative to the third, fourth, fifth . . . nth points or positions of the second body or combinations thereof.

From a different aspect, and in accordance with the invention, there is provided a dynamometer for determining the magnitude and direction of an applied force or moment. The dynamometer includes three spaced beam and bearing arrangements. Each of the arrangements includes a deflection beam and a support means. Platform means are disposed on and supported by the support means for receiving and being deflected by the applied force whereby deflection of the platform is transmitted to the deflection beams to cause deflection of the deflection beams. The beam and bearing arrangements isolate beam deflections to two mutually perpendicular directions, which mutually perpendicular directions are both perpendicular to the longitudinal axis of each deflection beam. Means are provided for measuring the deflection of the deflection beams in the two directions thereof. The deflection beams are arranged so that no two redundant directions of deflection of the deflection beams are permissible.

BRIEF DESCRIPTION OF DRAWINGS

The invention will be better understood by an examination of the following description, together with the accompanying drawings, in which:

FIG. 3 is a more detailed side view of the patient;

FIG. 4 is a front view of the leg showing motion module/digitizer attachment;

FIG. 5 is a rear view of the leg showing the electrogoniometer attachment;

FIG. 10 is a perspective view of a dynamometer in accordance with a further aspect of the invention;

FIG. 11 is a top view of FIG. 10;

FIG. 12 illustrates a beam and bearing arrangement of the inventive dynamometer;

DESCRIPTION OF PREFERRED EMBODIMENTS

Figure 1:
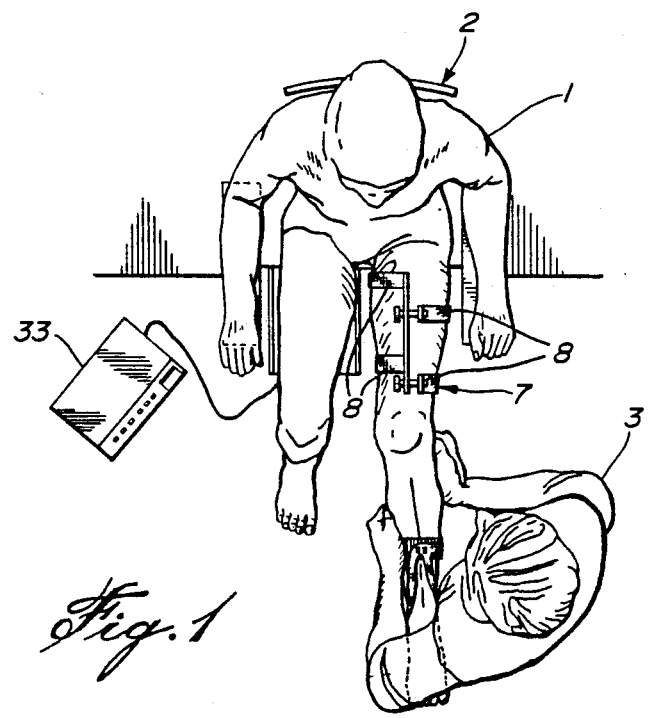
FIG. 1 is a three dimensional view of a patient, with KLE attached, being examined by a physician.
Figure 2:
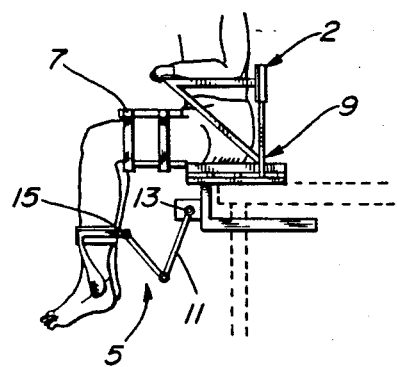
FIG. 2 is a side view of the patient.

Turning first to FIGS. 1 to 5, there is illustrated a patient 1 having the KLE attached and being examined by a physician 3. The KLE system includes a thigh restraint means 7, an instrumented seat 9 and a motion module 11. The motion module is connected at one end 13 to the instrumented seat which, as will be seen below, constitutes a fixed point or body. The other end 15 is connected to a second point or body. The purpose of the instrument is to determine the movement of the second point or body relative to the first point or body in three dimensional space.

The instrumented seat may be mounted on an examining table 17 and consists of a dynamometer 19 which measures applied forces. Instruments for measuring force are described in MEASUREMENT SYSTEMS: APPLICATION AND DESIGN by E. 0. Doebelin, McGraw Hill, pps 333–1350. The instrumented seat may also have an adjustable seat back arrangement 18 as is well known in the art.

The thigh restraint 7 comprises two or more pairs of off-set straps, which are fastened to each other by fastening means 8, and which displace soft tissue and may also provide a torquing of the tissue about the femur in order to minimize movement of the femur relative to the seat.

The lower leg attachment, illustrated best in FIGS. 4 and 5, comprises a strap member 21, for example a velcro strap on which is carried the attachment 15a for the end 15 of the motion module. The lower leg attachment functions by referencing the motion module to three bony prominences of the lower leg, namely, the tibial crest 23 and the medial and lateral malleoli, 25 and 27 respectively. Rollers 29 align themselves to the bony contours of the tibial crest, and balls in malleolar cups 31 do the same at the malleoli. These balls and rollers allow the skin to move between the attachment of the bone so that the attachment will move only with the bone which is important in attaining a true bone position measurement.

The system also includes a microprocessor based monitor 33 which receives outputs from the dynamometer and the motion module. Thus, the KLE is capable of sensing and measuring applied loads and displacements existing during the use of all standard knee evaluation techniques. In addition, the present KLE is designed to minimize the effects of soft tissue while still permitting the physician to hold, palpate and manipulate the joint as in normal procedures while the KLE provides accurate applied force and tibialfemoral motion readings in displayed and printed form.

The dynamometer force plate measures forces and moments in basic directions and permits the physician to know exactly to what levels the knee is being stressed. This is important when measuring laxity since the amount of relative bone motion depends on the stress applied. Knowledge of the forces is of utmost importance to the objective interpretation of joint laxity.

The motion module measures the true three dimensional position of the tibia relative to the seat, and hence, as the thigh is restrained, to the femur.

The motion module is an electromechanical device which functions on the principle that at least six measurements are required to totally define the position of an object in space as will be further discussed below. It will consist of a means capable of measuring six degree of freedom, three dimensional motion of one point or body relative to another point or body and preferably comprises a unique arrangement of electronic components capable of measuring rotational or translational displacements. A specific module is described below in association with FIGS. 6 to 8. Generally speaking, the two points or bodies between which relative motions are being measured are connected by a single rigid telescopic arm, or a single arm having a joint between its two ends.

The force measurement on the dynamometer is accomplished through the principles of opposite and equal reaction forces. The forces applied to the knee of the patient are reacted to by the femur and thigh which are in turn transmitted to the dynamometer. In as much as the forces are of a different arrangement in the dynamometer as compared to the knee, knowledge of the relative position of the relative position of the knee and the dynamometer, provided by the motion module, permits a theoretical interpretation of the forces and their representation in the co-ordinate system of the knee.

In operation, a patient is seated in the instrumented seat and the thigh of the leg of interest is restrained as shown in FIG. 1. The lower leg attachment is then mounted on the same leg as illustrated in the drawings, and the motion module is connected between the seat and the lower leg attachments. The physician can then twist the lower leg, and he will receive outputs indicating relative displacement as well as force applied.

Figure 7:
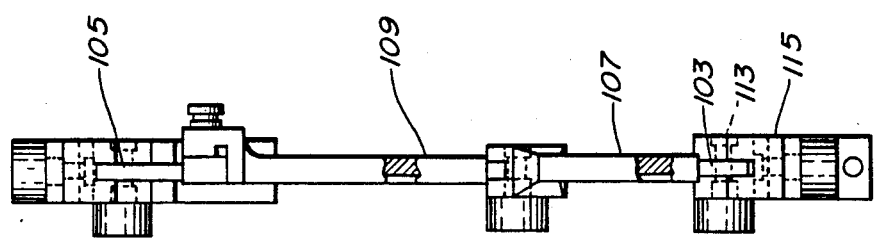
FIG. 7 is a side view of the combination.
Figure 6:
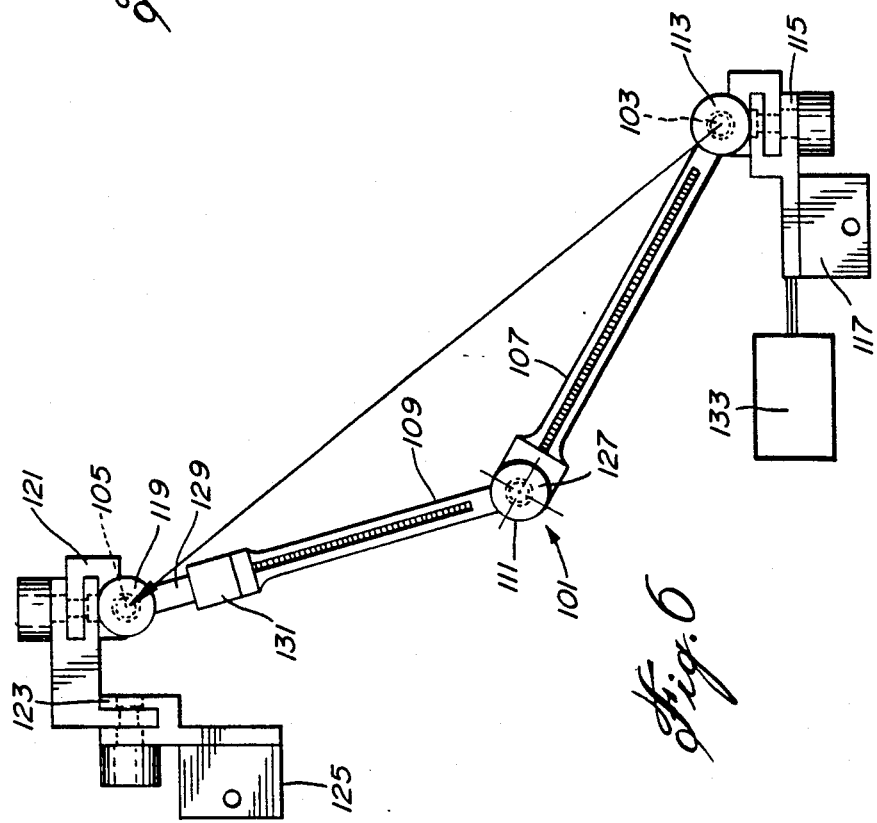
FIG. 6 is a front view of an electronic motion module/digitizer combination in accordance with the invention.
Figure 8A:
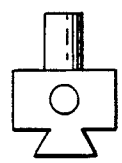
FIGS. 8A, 8B, 8C and 8D illustrate examples of inserts.
Figure 8B:
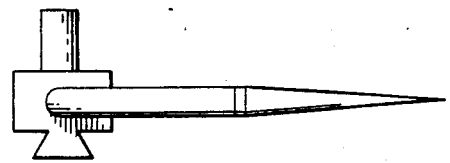
Figure 8C:
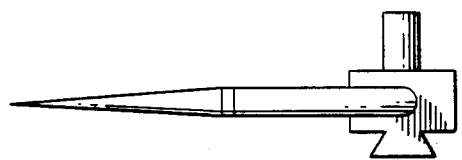
Figure 8D:
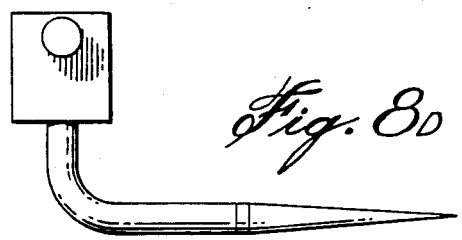
Figure 9:
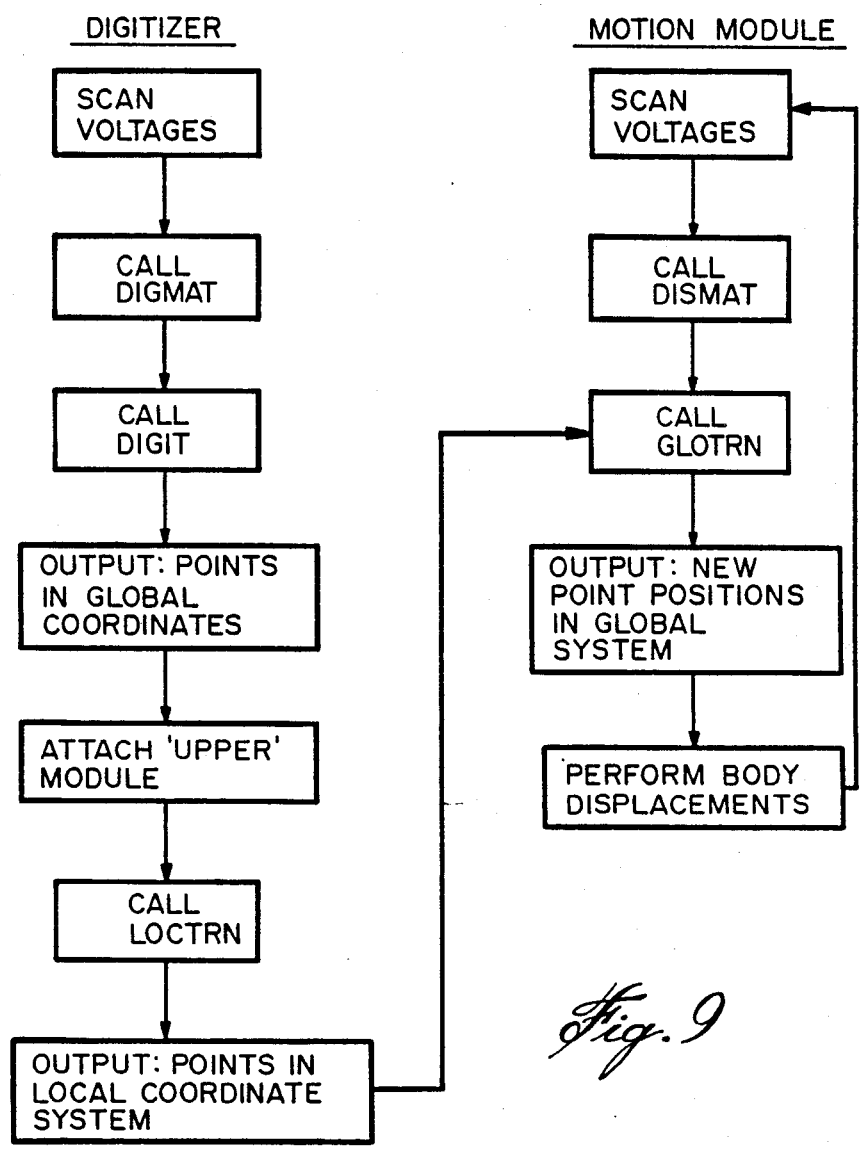
FIG. 9 is a flow chart of software for processing the electrical outputs of the combination to achieve the desired results.

Turning now to FIGS. 6 to 8, there is illustrated a particular motion module/digitizer combination which can be used in the KLE environment. However, as also mentioned, the combination can be used in other systems or it can be used independently. For example, it could be used in association with machine tools and other mechanical systems where it is necessary to be able to measure displacement of a first point or body relative to a second point or body.

To measure the motion of a body in three dimensional space, six unique measurements are required relating to the six degrees of freedom of motion in three dimensional space. The measurements can constitute six unique rotational measurements or six unique translational measurements or combinations thereof, i.e., four rotational and two translational, etc. The combination in accordance with the invention takes five unique measurements of rotational motion and one measurement of translational motion.

Referring now to FIGS. 6 and 7, the combination includes an elongated member 101 having a first end 103 and a second end 105. The elongated member comprises a first link arm 107 and a second link arm 109. The link arms 107 and 109 are joined together at 111 to permit relative translational movement as between 103 and 105 and to measure this translational movement. In the embodiments illustrated, the link arms are connected for pivotal motion whereby to permit relative translational motion of 103 and 105, and a rotary transducer means is used to measure this translational motion as will be discussed below.

As will be obvious, other means could be used for so connecting arms 107 and 109. For example, one of the arms could include a sleeve for overlying the other arm and for permitting movement of the other arm into and out of the sleeve. A translation transducer means could be included in the sleeve for measuring the translational motion.

Examples of rotary transducer means which can be used are resistive potentiometers, variable inductance transformers, syncro resolvers, inductance potentiometers and variable reluctance transducers. Examples of translational transducers which could be used are dial indicators, resistive potentiometers, variable inductance transformers, capacitance transducers, piezoelectric transducers, ionization transducers and optical transducers.

In describing the illustrated embodiment, rotary and translational potentiometers, respectively, are utilized. Accordingly, these will be henceforth referred to. However, it is to be understood that such translational and rotary potentiometers could be replaced by respective ones of the above-mentioned transducers.

Disposed at the end 103 is a first rotary potentiometer 113 which is disposed in line with the arm 103 and rotatable about an axis at right angles to the arm 103. A second rotary potentiometer 115 is disposed at right angles to the potentiometer 113 and is rotatable about an axis at right angles to the axis of the potentiometer 113. Potentiometer 115 is mounted on mounting block 117 for mounting the arrangement at one end thereof.

Disposed at second end 105 is a third rotary potentiometer 119 which is in line with the second link arm 109 and which rotates about an axis at right angles to the second link arm 109. A fourth rotary potentiometer 121 is disposed at right angles to potentiometer 119 and is rotatable about an axis at right angles to the axis of potentiometer 119. A fifth rotary potentiometer 123 is also disposed at right angles to potentiometer 119 and is rotatable about an axis at right angles to the axis of potentiometer 119. Potentiometer 123 is also at right angles to potentiometer 121 and its axis of rotation is also at right angles to the axis of potentiometer 121.

Potentiometer 123 is connected to mounting block 25 for mounting the arrangement at a second point.

In the illustrated embodiment, arms 107 and 109 are connected at 111 by a sixth rotary potentiometer 127 which is in line with both arms 107 and 109 and whose axis of rotation is at right angles to both arms 107 and 109.

The arrangement as thus far described can measure the motion in three dimensional space of end 105 relative to end 103 or vice-versa and is referred to as motion module. In accordance with the invention, there is provided the potential for digitizing the positions of third, fourth, fifth . . . nth points or bodies (henceforth, the use of the term points will be used and understood to refer to points or bodies) in three dimensional space, or combinations thereof, and of then measuring the motion or position of one of the points 103 or 105 relative to the position of the other point or relative to the third, fourth, fifth . . . nth points, or positions of the second body, or combinations thereof. This potential is achieved by making one of the link arms disconnectable from its respective mounting block and reconnectable again thereto. In the illustrated embodiment, link arm 109 is disconnectable from mounting block 125. Specifically, the protrusion 129 which extends from potentiometer 119 is insertable into a receptacle 131. The protrusion is also removable from the receptacle, and other inserts, such as those illustrated in FIGS. 8A, 8B, etc. can be inserted into the receptacle for digitizing the positions of other points in space.

For an understanding as to how the combination operates, we will take the intersection of the axes of potentiometers 113 and 115 as the global origin O. Thus, potentiometers 113, 115 and 127 define a spherical co-ordinate system about O. Specifically, potentiometers 113 and 115 provide the conventional angles $\Theta$ and $\Phi$ respectively, while the potentiometer 127, combined with 107 and 109, provide the length of the vector R. (Knowing the length of 107 and 109, and knowing the angle therebetween, it is quite easy to determine the length of the vector R). Point B is defined as the intersection of the axes of potentiometers 119, 121 and 123 and is considered the origin of the "moving body" coordinate system. In distinction thereto, O is considered the origin of a "fixed" body or co-ordinate system. Specifically, mounting block 125 would be mounted on a moving body. Mounting block 117 would be mounted on the fixed body or co-ordinate system, and the measurement of the movement of 105 relative to 103 would define the motion of the moving body relative to the fixed body or co-ordinate system.

The final description of the moving body motion is contained in the three finite rotations provided by the potentiometers 119, 121 and 123.

To illustrate how the combination is used as a digitizer, the protrusion 119 is removed from the receptacle 131, and one of the digitizer tips illustrated in FIG. 8 is inserted into the receptacle in place of the protrusion 119. The tip is then pointed at points of interest, namely, a third, fourth, fifth . . . nth points above-mentioned, and a reading is taken of the three dimensional position in space of these points.

As will be understood, conductive leads from the potentiometers will be brought to a connecting board, which could be disposed on the mounting blocks 117, so that the electrical signals developed at the potentiometers can be brought to a processing means such as the processing means illustrated schematically at 133 in FIG. 1. It will, of course, be necessary to provide DC power to the potentiometer to measure the changing resistance thereof, as well known in the art, and this DC power could also be provided from the processing means 133.

The potentiometers will provide the data for determining the extent and direction of the motion of point 105. In order to determine the direction and extent, the data must be processed. Preferably, the data is processed by computer means. A flow chart for controlling such a computer is illustrated in FIG. 8.

Three basic subroutines are employed in digitization, two of which are illustrated in the flow chart. The DIGMAT (digitization transformation matrix) and DIGIT (digitization) are shown in the flow chart while the NEWTIP (support routine for user defined tip) must be provided by the user and takes into account the dimensions and shape of the user supplied tip.

While the user must write a program employing the subroutines in a manner appropriate to his specific application, in all cases the following procedure must be used.

The protrusion 129 is removed from the receptacle 131, and one of a variety of tips is inserted in the receptacle. The mounting blocks 117 must be firmly mounted at a position which both permits easy access to most points of interest and is also appropriate for any subsequent motion measurement using both upper and lower components of the motion module. A position of interest is then pointed at with the tip.

The physical characteristics are inputted into the computer memory, and a code is then presented to the computer to let it know which of the tips is being used.

Upon pointing at the position with the tip, the program must be activated either through a remote switch or a keyboard entry. The control program will then scan the signals in the potentiometer, and then, in sequence, call the subroutine DIGMAT, which uses as input the voltage values of potentiometers 113, 115 and 127, as well as the voltage of the power supply. DIGMAT outputs to transformation matrices which are used in the subroutine digit which is the next subroutine to be called. DIGIT actually computes the position of DTIP in the global coordinate system using as input the output of DIGMAT and DTIP coordinates in potentiometer 127 coordinate system.

An output is then provided of the points in the global coordinate system, that is, relative to the point O.

This procedure is repeated until all of the points of interest have been digitized. The TIP is then removed from the receptacle 131 and the protrusion 129 is again inserted in the receptacle. The subroutine LOCTRN, which computes the coordinates of the digitized points in the local coordinate system (that is, with the point B as an origin) is then called. These points are then outputted to the GLOTRN subroutine which will be discussed below.

In the meantime, the mounting block 125 would have been attached to a point of interest. Displacements of this point are perfomred, and the potentiometer signals are once again scanned. This data is communicated to the computer and the subroutine DISMAT is called. DISMAT computes the contents of the transformation matrix describing the body in three dimensional space. The subroutine GLOTRN is then called and outputs new positions of those points previously digitized on the body or analytically generated points, in the global system. This procedure continues as the point of interest moves through different positions.

The following are the technical specifications of the subroutines:

SUBROUTINE DIGMAT (DVOL, DT12, DT3)

DESCRIPTION

This subroutine computes matrix DT12 as well as matrix DT3 which locates the position of potentiometer-113 and potentiometer-127 coordinate systems, respectively.

These two matrices are strictly inputs to subroutines DIGIT and NEWTIP, and have no significance to the user.

INPUT

DVOL (4), voltages of potentiometers 115, 113 and 127, and the power supply, respectively. (Note 1)

OUTPUT

DT12 (3,3) and DT3 (3,3) are the abovementioned matrices. (Note 1)

NOTE 1-all the variable names starting with D in each subroutine, are double precision.

SUBROUTINE DIGIT (DT12, DT3, DTIP, DPNTRF)

DESCRIPTION

This subroutine computes the coordinates of the digitizer tip with respect to the global coordinate system.

INPUT

DT12 (3,3), and DT3 (3,3) locate the position of potentiometer-113 and potentiometer-127 coordinate systems, respectively. (Refer to subroutine DIGMAT). (Note 3)

DTIP (3) are the coordinates of the tip in use with respect to the potentiometer-127 coordinate system. (Note 1, 2 & 3)

OUTPUT

DPNTRF (3) are the coordinates of the tip with respect to the global coordinate system. (Note 2 & 3)

NOTES

1-The coordinates of the digitizer tips are provided as part of the Digitizer Unit. For the coordinates of User tip, use subroutine NEWTIP. (Refer to subroutine NEWTIP)

2-In all coordinate arrays 1, 2 & 3 are X, Y and Z coordinates, respectively. (e.g. DTIP(1)=X coordinate)

3-All variable names starting with D are in Double Precision

SUBROUTINE NEWTIP (DT12, DT3, DPNTRF, DTIP)

DESCRIPTION:

The main purpose of this subroutine is to define the coordinates of any user-designed tip with respect to potentiometer-127 coordinate system without independently measuring the tip dimensions. In order to find the tip constants, first mount tip number 1 see 8b) and touch a point (Note 1). Then mount the new tip and touch the same point. Through the software the coordinates of the point are computed by tip #1 and are used to compute the constants for the new tip (Refer to the Control Program Flow Chart).

NOTES

1-For best results, use a point within 6 to 8 inches from the base of the digitizer.

INPUT

DT12 (3,3), and DT3 (3,3) locate the position of potentiometer-113 and potentiometer-127 coordinate systems, respectively (Note 1)

DPNTRF(3) : coordinates of the digitized point by tip #1 with respect to global coordinate system. (Note 1 & 2)

OUTPUT

DTIP(3) : coordinates of the tip with respect to potentiometer-127 coordinate system, or better known as the new tip constants. (Note 1 & 2)

NOTES

1-All variable names starting with D are double precision.

2-In the coordinate system arrays 1, 2 & 3 are X, Y and Z coordinates, respectively.

SUBROUTINE DISMAT (DVOL, DMAT2)

DESCRIPTION

DISMAT computes the position of the local coordinate system with respect to the global coordinate system. The local coordinate system is in line with indicated edges of upper mounting block.

INPUT

DVOL(7) voltage readings of potentiometers-113, 127, 115, 119, 121, 123 and the power supply line, respectively. (Note 1)

OUTPUT

DMAT2 (4,3) consists of: DMAT2(4,1,) DMAT2 (4,2) and DMAT2 (4,3) are the coordinates of point B in global coordinate system.

DMAT2 (3,3) defines the position of the local coordinate system with respect to the global coordinate system. (Note 1) DMAT 2 (4,3) is input only to subroutines LOCTRN and GLOTRN, and has no significance to the user.

NOTE

1-All variable names starting with D are double precision.

SUBROUTINE LOCTRN (DMAT2, DPOINIT, DPNTLC, N)

DESCRIPTION

LOCTRN computes the coordinates of the digitized points in local coordinate system.

These coordinates are constant as long as the upper mounting block is fixed to the bone or some other chosen mounting base.

If the upper mounting block is shifted these coordinates should be computed again by calling subroutine LOCTRN. (Refer to the Control Program Flow Chart)

INPUT

DMAT2 (4,3), from subroutine DISMAT (refer to subroutine DISMAT) (Note 1)

N is number of points; integer.

DPOINT (3,N) : coordinates of the digitized and analytical points in the global coordinate system. (Note 1 & 2)

OUTPUT

DPNTLC (3,N) coordinates of the points with respect to the local coordinate system. (Note 1 & 2)

NOTE

1-All variable names starting with D are double precision.

2-In the coordinates arrays 1, 2 and 3 are X, Y and Z coordinates, respectively.

SUBROUTINE GLOTRN (DAMT2, DPNTLC, DPNTGL, N)

DESCRIPTION:

GLOTRN computes the new coordinates of the points in the global coordinate system.

INPUT

DMAT2 (4,3), from subroutine DISMAT (refer to subroutine DISMAT). (Note 1)
N number of points; integer.
DPNTLC (3,N) : coordinates of the points in local coordinate system. (Note 1 & 2)

OUTPUT

DPNTGL (3,N) new coordinates of the points in global coordinate system. (Note 1 & 2)

NOTES

1-All variable names starting with D are double precision.
2-In the coordinate arrays 1, 2 and 3 are X, Y and Z coordinates, respectively.

Although reference was made to dynamometers above, in accordance with a further aspect of the invention, there is provided a novel dynamometer, comprising a triple beam and bearing arrangement illustrated in FIGS. 10 to 14 hereof. As seen in these Figures, the dynamometer comprises a supporting frame 201 which, in the illustrated embodiment, comprises a four walled structure. Disposed centrally of one wall is a beam and bearing arrangement 203. Second and third beam and bearing arrangements 205 and 207 are disposed in the corners opposite the wall of the 203 arrangement.

Supported at the top surfaces of the arrangements 203, 205 and 207 is a platform 209 (only partially shown in FIG. 10) which is fixedly attached to the arrangements 203, 205 and 207 by bolts 204, 206 and 208 as will be more fully described below.

As seen in FIG. 12, each beam and bearing arrangement consists of a deflection beam 211. The deflection beam 211 is illustrated as being cylindrical in shape in FIG. 12. However, as will be appreciated, the deflection beam could be some other shape, for example, it could be rectangular in cross-section.

Each arrangement 203, 205 and 207 further includes a spherical/linear bearing arrangement, illustrated generally at 213, and including a linear bushing 215 and a spherical bearing 217 which comprises a sphere member 219 and a casing 221.

The top end of the casing 221, which comprises the support means for, for example, a platform, includes a shoulder 214 (see FIG. 12) for carrying a member which could be, for example, the platform 209 (see FIG. 10). A threaded portion 218 extends upwardly from the shoulder 214 and through the member. A bolt, which corresponds with bolts 204, 206 and 208 in FIG. 11, is screwed onto the end of threaded member 218 to fixedly attach the member 209 to the spherical bearing 217.

In a like manner, the platform 209 will be fixedly attached to the top ends of the respective casings of arrangements 203, 205 and 207 in FIGS. 10 and 11 so that the deflection beams of the respective arrangements 203, 205 and 207 are connected to the platform via their respective spherical/linear bearing arrangements.

Considering now the effect of a force on member 209 in FIG. 10, the force is transmitted through member 209 to a beam and bearing arrangement e.g. beam and bearing arrangement 217 of FIG. 12 such that the component of this force in the X direction (perpendicular to the longitudinal axis of deflection beam 211) will cause flexure of the deflection beam 211 in the X direction, and the component of the force in the Y direction (perpendicular to the X direction) will cause flexure of the deflection beam 211 in the Y direction. However, the Z component of the force will merely cause the spherical bearing to move along the deflection beam 211 against only negligible resistance, and the components of the force causing rotation about the X, Y and Z axes will merely cause rotation of the spherical bearing 217 about those respective axes, so that the latter components will neither cause flexure of the deflection beam 211 nor will they be absorbed. Instead, the latter components will be released for measurement by the other beam and bearing arrangements in their respective X and Y directions only.

The deflection beams of the arrangements 203, 205 and 207 are arranged such that the longitudinal (Z) axis of each deflection beam is the perpendicular bisector of the respective side of an equilateral triangle. This particular arrangement is convenient for analysis.

Although the platform illustrated in FIGS. 10 and 11 is rectangular in shape, this particular shape is not necessary. Any convenient shape is acceptable as long as the platform can be supported by the three spherical bearings and can be attached to the bearings such that the distance between the bearing centers maintains an equilateral triangle (e.g. the platform may be triangular with corners at the positions of bolts 204, 206 and 208). Each deflection beam is then perpendicular to the side of the triangle opposite its corner. All external forces desired to be measured are applied to the platform 209. These forces result in the deflection of the deflection beams as abovedescribed. The deflections are measured as an indication of the forces as will be discussed below.

Although in the illustrated embodiment the beam and bearing arrangements are at the corners of an equilateral triangle, any arrangement of the three beam and bearing arrangements is acceptable as long as such arrangement does not result in two redundant directions of deflection. Such arrangements are acceptable for two reasons:

(A) such an arrangement will provide a rigid mechanical mechanism; and
(B) the minimum of six non-redundant forces required for the solution of the equilibrium equation will be measured.

Returning to FIG. 12, each deflection beam is fixedly held, in a cantilever fashion, in a deflection beam restraining support 222.

Returning to FIGS. 10 and 11, associated with each beam and bearing arrangement 203, 205 and 207 is a detector system consisting of detector support frames 223, 225 and 227 associated with the arrangements 203, 205 and 207 respectively. Detector means, represented schematically at 229 and 231, extend from the deflection beam of the arrangement 207 to platform 227 in the flexure directions of the deflection beam. Similarly, detectors 233 and 235 are associated with the deflection beam of the arrangement 203 in the deflection directions thereof, and detectors 237 and 239 are associated with the deflection beam of the arrangement 205 in the deflection directions thereof. Support blocks 241 and 243 correspond with block 222 in FIG. 12, while the deflection beam of arrangement 203 is retained in side wall 245 which also performs the same function as the block 222 of FIG. 12.

Figure 13:
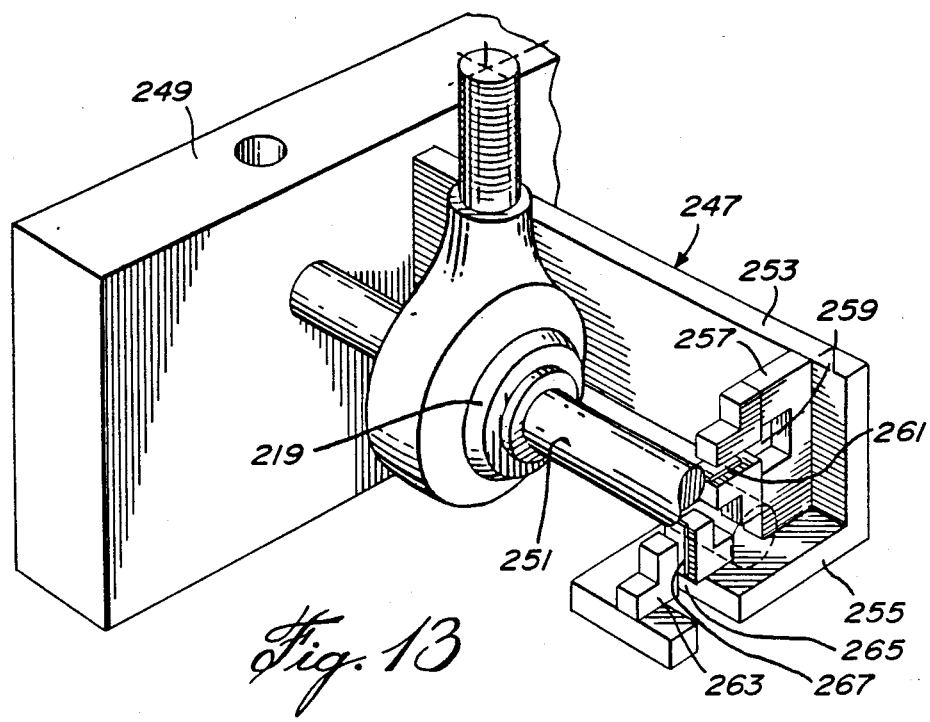
FIG. 13 is a perspective view of a detector arrangement.
Figure 14:
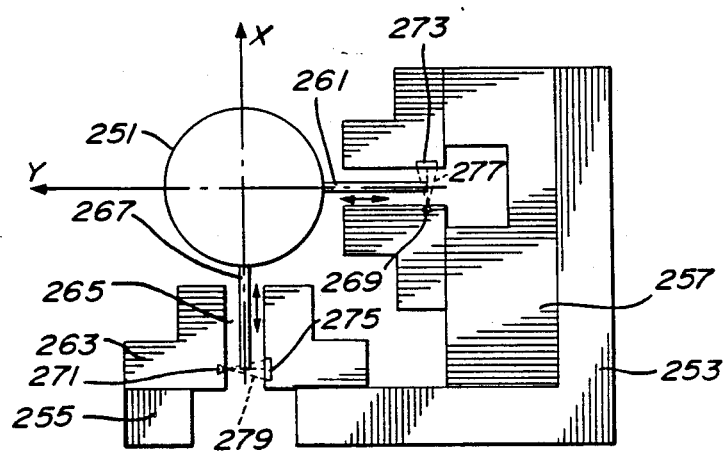
FIG. 14 is an end view of FIG. 13.

Turning now to FIGS. 13 and 14, a support frame for a detector system illustrated generally at 247 is associated with a support block 249 (similar to block 222 of FIG. 12), and a deflection beam 251 (corresponding with deflection beam 211 of FIG. 12). The frame consists of a vertical wall 253 and a bottom wall 255 which is at right angles to wall 253. Extending from wall 253 is a light beam arrangement 257, which includes an aperture 259, and a light beam interrupter 261 which is attached to the deflection beam 251 and extends along the Y axis into the aperture 259. In a like manner, a light beam arrangement 263 extends from wall 255 and includes an aperture 265. Light beam interrupter 267, attached to deflection beam 251 and extending in the X direction thereof, extends into the aperture 265.

As best seen in FIG. 14, on a leg on one side of aperture 259 is mounted a light emitting element 269 such as, for example, an LED. Similarly, a light emitting element 271 is mounted on a leg on one side of the aperture 265.

Mounted on the leg on the other side of aperture 259 is a light receiving element 273, for example, a phototransistor. Similarly, light receiving element 275 is mounted on the leg on the other side of aperture 265.

In accordance with the invention, the light emitting elements 269 and 271 form conical light beams 277 and 279 respectively. In accordance with the illustrated arrangement, interrupter 261 interrupts a portion of light beam 277 whereas interrupter 267 interrupts a portion of light beam 279 when deflection beam 251 is in its rest position. If deflection beam 251 is deflected only in the Y direction, interrupter 261 will move across light beam 277 so that a greater (or lesser) portion of light beam 277 will be blocked. However, interrupter 267 will move along light beam 279, rather than into or out of (across) it, so that deflection in the Y direction will not affect the measurements in the X direction. Similarly, a greater or lesser portion of only light beam 279 will be interrupted when deflection beam 251 is deflected in only the X direction. Accordingly, the illustrated detector system eliminates cross talk between the two directions (X and Y) of any particular deflection beam.

Although the illustrated detector system uses light beams and interrupters, other conventional displacement transducers are also possible. Such other transducers would include:
Capacitance gauge
Linear variable differential transformer (LVDT)
Hall effect transducer
Rectilinear potentiometer.

When the force is applied to the platform 209, depending on the magnitude of the force and the direction of the application thereof, the deflection beams of arrangements 203, 205 and 207 will be deflected by different amounts. The magnitudes of deflection of each deflection beam are resolved in two directions only as above-described, and the magnitudes in the respective directions are measured by the devices 229, 231, 233, 235, 237 and 239. This will provide measurements of six unique components of the applied force. Using this technology and well known mathematical vector transformations, the force applied at the platform can be calculated.

It can be seen that, with the dynamometer as described, and especially because of the linear spherical bearing arrangements, only six measurements are needed to calculate the magnitude and direction of applied forces or moments, and that there is no crosstalk between the measurement directions of each deflection beam.

Although several embodiments have been described, this was for the purpose of illustrating, but not limiting, the invention. Various modifications, which will come readily to the mind of one skilled in the art, are within the scope of the invention as defined in the appended claims.

We claim:

1. A dynamometer for determining the magnitude and direction of an applied force or moment comprising:
   three spaced beam and bearing arrangements;
   each of said arrangements comprising a deflection beam and support means;
   platform means, disposed on and supported by said support means, for receiving and being deflected by said applied force;
   whereby, deflection of said platform is transmitted to said deflection beams to cause deflection of said deflection beams;
   said beam and bearing arrangements isolating beam deflections to two mutually perpendicular directions, which mutually perpendicular directions are both perpendicular to the longitudinal axis of each said deflection beam;
   means for measuring the deflection of said deflection beams in said two directions thereof;
   wherein, said deflection beams are arranged such that no two redundant directions of deflection of said deflection beams are permissible.

2. A dynamometer as defined in claim 1 wherein each said beam and bearing arrangement comprises:
   a linear bushing on the respective deflection beam providing negligible resistance to sliding along the beam; and
   a spherical bearing around the linear bushing providing negligible resistance to bearing housing rotation about the center of said deflection beam.

3. A dynamometer as defined in claim 2 wherein each said spherical bearing comprises a bearing housing;
   said platform being fixedly attached to the top ends of said bearing housings which comprise said support means.

4. A dynamometer as defined in claim 3 wherein said means for measuring the deflection of said deflection beams comprises, for each said deflection beam, a first measuring means for measuring the deflection in a first direction of each said deflection beam perpendicular to the longitudinal axis of said deflection beam; and
   a second means for measuring the deflection of each said deflection beam in a second direction perpendicular to said first direction.

5. A dynamometer as defined in claim 4 wherein said deflection beams are arranged such that the longitudinal axis of each deflection beam is the perpendicular bisector of a respective side of an equilateral triangle.

6. A dynamometer as defined in claim 5 xand including a four-walled square support frame;
   one of said beam and bearing arrangements being mounted adjacent the center of one of the walls of the support frame;

the other two beam and bearing arrangements being mounted, respectively, adjacent corners of said support frame opposing said one wall.

7. A dynamometer as defined in claim 6 wherein said means for measuring comprises, for each said deflection beam, a detector system;

each said detector system comprising:

a vertical wall extending along and parallel to the respective deflection beam;

a bottom wall extending at right angles to the vertical wall and below said deflection beam;

first aperture support means extending from said vertical wall such that said first aperture extends towards said deflection beam and second aperture support means extending from said bottom wall such that said second aperture extends towards said deflection beam;

a first conical light beam extending across said first aperture and a second conical light beam extending across said second aperture;

first light interrupter means connected to said deflection beam and extending into said first aperture across said first conical light beam and second light interrupter means connected to said deflection beam and extending into said second aperture across said second conical light beam.

* * * * *